(12) United States Patent
Eikel et al.

(10) Patent No.: US 8,445,842 B2
(45) Date of Patent: *May 21, 2013

(54) MECHANICAL HOLDER FOR SURFACE ANALYSIS

(75) Inventors: Daniel Eikel, Trumansburg, NY (US); John D. Henion, Trumansburg, NY (US); Christopher Alpha, Ithaca, NY (US); Jason Scott Vega, Ithaca, NY (US)

(73) Assignee: Advion, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,358

(22) Filed: Jul. 30, 2012

(65) Prior Publication Data

US 2012/0288423 A1 Nov. 15, 2012

Related U.S. Application Data

(63) Continuation of application No. 13/100,383, filed on May 4, 2011, now Pat. No. 8,294,087.

(60) Provisional application No. 61/333,956, filed on May 12, 2010.

(51) Int. Cl.
*G01N 1/00* (2006.01)
*G01N 1/28* (2006.01)
*H01J 49/26* (2006.01)

(52) U.S. Cl.
USPC ........ 250/281; 250/288; 250/428; 73/864.91; 436/174; 422/527; 422/561

(58) Field of Classification Search
USPC ........ 250/281, 288, 428; 73/864.91; 436/174; 422/527, 561
See application file for complete search history.

(56) References Cited

U.S. PATENT DOCUMENTS

| | | | |
|---|---|---|---|
| 5,508,200 | A | 4/1996 | Tiffany et al. |
| 5,895,704 | A | 4/1999 | Lerch et al. |
| 5,962,729 | A | 10/1999 | Hayden et al. |
| 6,036,659 | A | 3/2000 | Ray et al. |
| 6,258,045 | B1 | 7/2001 | Ray et al. |
| 7,238,531 | B2 | 7/2007 | Chace |
| 7,611,670 | B2 | 11/2009 | Wandell et al. |
| 7,798,865 | B2 | 9/2010 | McCoy et al. |
| 8,294,087 | B2 * | 10/2012 | Eikel et al. ............ 250/282 |
| 2011/0129863 | A1 * | 6/2011 | Shoemaker et al. ........ 435/29 |
| 2011/0133077 | A1 * | 6/2011 | Henion et al. ............ 250/288 |
| 2011/0269166 | A1 * | 11/2011 | Van Berkel et al. ........ 435/29 |

* cited by examiner

*Primary Examiner* — Nikita Wells
(74) *Attorney, Agent, or Firm* — Fish & Richardson P.C.

(57) ABSTRACT

A mechanical holder that provides for a confined sampling region for extraction and removal of chemical substances contained in a dried blood spot or other spot of sample is described herein.

20 Claims, 4 Drawing Sheets

MECHANICAL HOLDER FOR SURFACE ANALYSIS

CROSS-REFERENCE TO RELATED APPLICATIONS

This is a continuation of U.S. application Ser. No. 13/100,383 filed May 4, 2011, which claims the benefit under 35 U.S.C. §119(e) of U.S. Provisional Application Ser. No. 61/333,956, filed on May 12, 2010, the contents of each of which are hereby incorporated by referenced herein in its entirety as if fully set forth herein.

BACKGROUND

Mass spectrometry is an analytical process that identifies the chemical composition of a compound or sample based on the mass-to-charge ratio of charged particles derived from the compound or sample. In general, in mass spectrometry, a sample undergoes ionization to form charged particles (ions). The ratio of mass-to-charge of the particles is determined by passing them through electric and/or magnetic fields in a mass spectrometer.

In some mass spectrometer systems, molecules can be analyzed in a quadrupole mass spectrometer using "electrospray" ionization to introduce the ions into the spectrometer. In electrospray ionization a spray needle may be positioned near to the entrance orifice of a quadrupole, magnetic, ion trap, Fourier transform mass spectrometer (FTMS), orbitrap, or time-of-flight (TOF) mass spectrometer, or close to the entrance of a capillary leading to a vacuum entrance orifice of the quadrupole or other type of mass spectrometer. A dilute solution, including the molecules of interest, is pumped through the electrospray needle or emitter and an electric potential between the needle or emitter orifice and a vacuum orifice (e.g., a reference electrode) leading to the mass analyzer forms a spray ("electrospray") of the solution.

SUMMARY

Dried blood spots (DBS) or dried matrix spots (DXS) where X can be any sample type on an sample card such as paper or other substrate surfaces are viewed as an alternative to the conventional methods of collecting, transporting, and storing biological samples such as urine, plasma, saliva and feces as well as milk and other samples of interest. A mechanical holder that provides for a confined sampling region for extraction and removal of chemical substances contained in a dried matrix spot with direct analysis of the extracted sample is described herein. Methods for analyzing a dried matrix spots such as dried blood spots are also described herein.

In some aspects, a method of extracting analytes from a sample card includes placing a sample card that includes a dried sample in a lower portion of a device configured to house the sample card and lowering an upper portion of the device mechanically connected to the lower portion, the upper portion including one or more fittings with each fitting defining an opening in the upper portion and including a rigid lower edge. The method also includes engaging one or more locking mechanisms to compress the sample card substantially uniformly between the rigid lower edge of the one or more fittings and the lower portion to form a substantially liquid tight seal around a portion of the sample card. The method also includes introducing a solvent into a solvent delivery device, dispensing the solvent to contact a surface of the sample card, and aspirating the solvent and dissolved analytes into the solvent delivery device from the surface of the sample card. The method also includes interfacing the solvent delivery device to an automation device to deliver the solvent delivery device to an ion sprayer and directing ions from the ion sprayer to a mass analyzer.

Embodiments can include one or more of the following:

The sample card can be a dried blood spot card.

The method can also include repeating the steps of dispensing and aspirating prior to interfacing the solvent delivery device to an automation device to deliver the solvent delivery device to the ion sprayer.

The method can also include repeating the steps of dispensing and aspirating at the same location on the sample prior to interfacing the solvent delivery device to an automation device to deliver the solvent delivery device to the ion sprayer.

Dispensing the solvent can include dispensing microliters of solvent from the first end of the solvent delivery device to contact the sample.

Engaging one or more locking mechanisms can depress the sample card by between about 0.015 inch to about 0.030 inch to form the substantially liquid tight seal.

Engaging one or more locking mechanisms can depress the sample card by between about 0.010 in to 0.100 in to form the substantially liquid tight seal.

Engaging one or more locking mechanisms can depress the sample card by between about 0.025 inch to about 0.1 inch to form the substantially liquid tight seal.

Engaging one or more locking mechanisms can include tightening one or more screws.

Dispensing the solvent can include forming a liquid junction between a sample surface of the sample card and the solvent delivery device.

Dispensing the solvent can include wetting a surface of the sample card.

Engaging the one or more locking mechanisms can include engaging multiple locking mechanisms to apply a substantially uniform pressure onto sample substrate surface by the upper portion.

In some additional aspects, a system can include a lower portion configured to house a sample card that includes a dried sample, an upper portion mechanically connected to the lower portion, the upper portion including one or more fittings each defining an opening in the upper portion configured to receive a solvent delivery device and including a rigid lower perimeter edge, and one or more locking mechanisms configured to compress the sample card between the rigid lower perimeter edge of the one or more fittings and the lower portion to form a substantially liquid-tight seal around a portion of the sample card when the upper portion and the lower portion are in a closed position and the locking mechanisms are engaged.

Embodiments can include one or more of the following:

The solvent delivery device can be capable of delivering an extraction solvent for extracting chemicals from the sample substrate material.

The solvent delivery device can be a pipette tip.

The solvent delivery device can be an extraction tip.

The fitting can be a PEEK, polymer, brass or stainless steel with a rigid lower circular perimeter edge capable of making a leak-tight seal when clamped down upon the sample card without cutting a disk from the sample card.

The upper portion can include at least four fittings in an array.

The upper portion can include 96 fittings in an array.

The upper portion can include between four and 96 fittings in an array.

The system can also include a robotic device configured to extract analytes from the substrate to form a solution from a surface of the sample card using a solvent delivery device which can then be withdrawn from the surface and delivered to a mass spectrometer.

The fitting can be configured such that the extraction solvent introduced into the fitting is substantially confined within the walls of the fitting.

Confining the extraction solvent within the walls of the fitting can preclude the need to employ hydrophobic spray chemicals to preclude said dispersion.

The liquid-tight seal can be configured to confine at least 90% of the extraction solvent within the walls of the fitting.

The liquid tight seal can be configured to confine at least 95% of the extraction solvent within the walls of the fitting.

The liquid tight seal can be configured to confine at least 98% of the extraction solvent within the walls of the fitting.

In some additional aspects, a system includes a lower portion configured to house a sample card and an upper portion mechanically connected to the lower portion, the upper portion including a fitting or an array of fittings configured such that when the upper portion and the lower portion are in a closed position, a substantially liquid-tight seal is formed around a portion of the sample card.

Embodiments can include one or more of the following:

The solvent delivery device can be capable of delivering an extraction solvent for extracting chemicals from the sample substrate material.

The solvent delivery device can be a pipette tip.

The solvent delivery device can be an extraction tip.

The fitting can be a PEEK, polymer, brass or stainless steel with a rigid lower circular perimeter edge capable of making a leak-tight seal when clamped down upon the sample card without cutting a disk from the sample card.

The upper portion can include at least four fittings in an array.

The system can also include a robotic device configured to extract analytes from the substrate to form a solution from a surface of the sample card using a solvent delivery device which can then be withdrawn from the surface and delivered to a mass spectrometer.

The fitting can be configured such that extraction solvent introduced into the fitting is substantially confined within the walls of the fitting.

Confining the extraction solvent within the walls of the fitting can preclude the need to employ hydrophobic spray chemicals to preclude said dispersion.

The liquid tight seal can be configured to confine at least 75% of the extraction solvent within the walls of the fitting.

The liquid tight seal can be configured to confine at least 90% of the extraction solvent within the walls of the fitting.

The liquid tight seal can be configured to confine at least 95% of the extraction solvent within the walls of the fitting.

The liquid tight seal can be configured to confine at least 98% of the extraction solvent within the walls of the fitting.

DESCRIPTION OF THE DRAWINGS

Like reference symbols in the various drawings indicate like elements.

DESCRIPTION

Dried blood spots (DBS) or dried matrix spots (DXS) where X can be any sample type on an sample card such as paper or other substrate surfaces such as dried blood spots (DBS) on a paper or other substrate surfaces are viewed as an alternative to the conventional methods of collecting, transporting, and storing biological samples such as urine, plasma, saliva and feces as well as milk and other samples of interest. A mechanical holder that provides for a confined sampling region for extraction and removal of chemical substances contained in/on the surface. The extracted substances can be analyzed using a mass spectrometer.

Figure 1A:
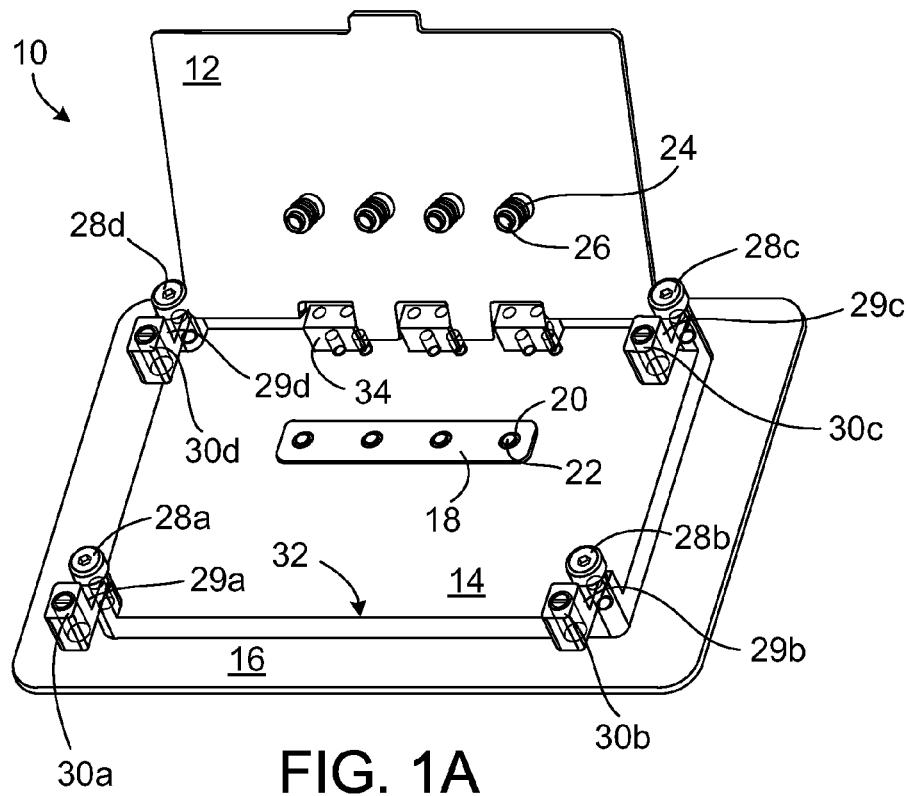
FIGS. 1A, 1B, and 1C show an exemplary mechanical holder system.
Figure 1B:
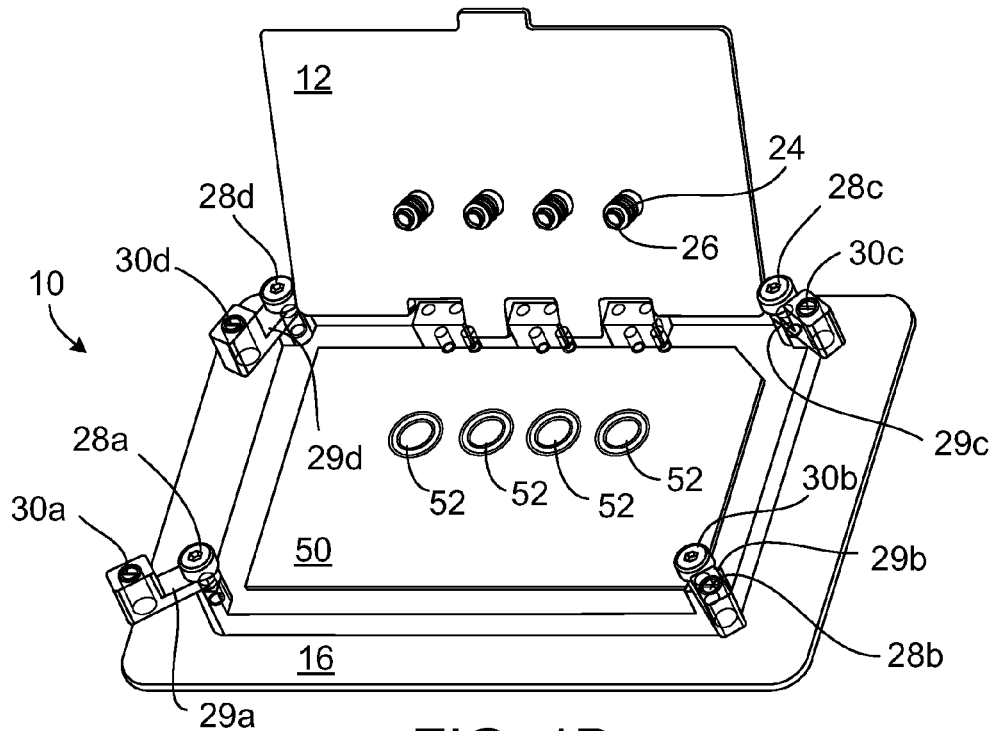
Figure 1C:
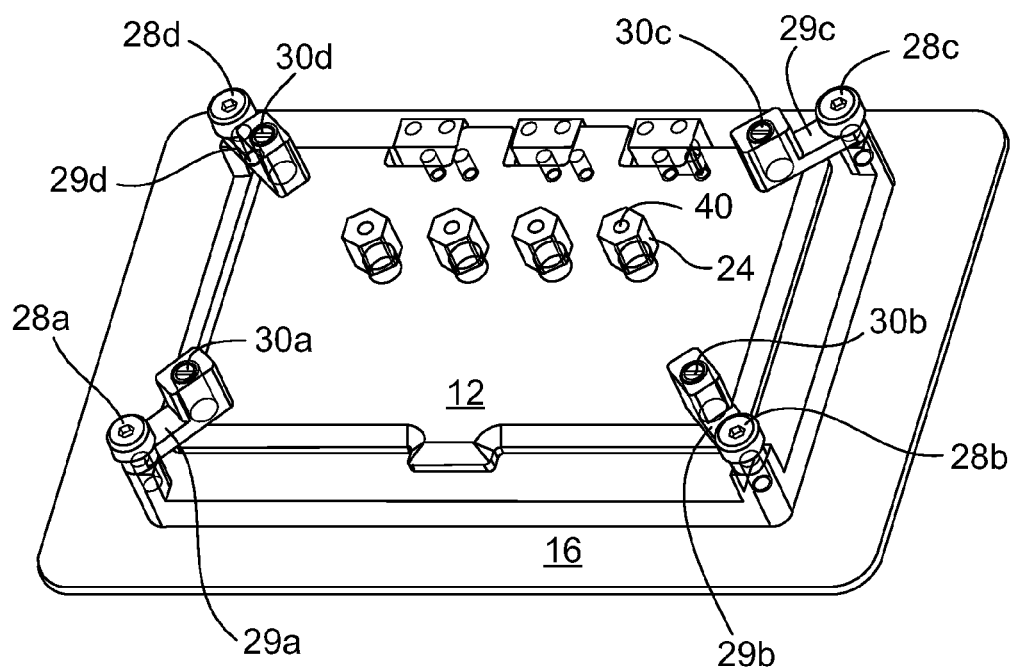

FIGS. 1A-1C show a mechanical holder system 10 that provides a confined sampling region for extraction and removal of chemical substances or samples collected and stored on a variety of disposable, single use collection substrates such as a dried matrix spot included on a substrate such as a substrate formed of paper or similar absorbent or non-absorbent substrate material. The mechanical holder system 10 forms a region in which a micro liquid junction between a solvent delivery device (e.g., a pipette tip or extraction tip that includes SPE sorbent material) and a porous surface such as a cellulose or cotton-based card or suitable polymeric membrane material and provides a method for solvent extraction from the defined, constrained region. The mechanical holder system enables analysis of a sample extracted from the collection substrate, for example by a mass spectrometer. More particularly, FIG. 1A shows the mechanical holder system 10 in an open position, FIG. 1B shows the mechanical holder system 10 in an open position with a collection substrate placed in the holder system 10, and FIG. 1C shows the mechanical holder system 10 in an closed position.

The mechanical holder system 10 includes a lower bed portion 16 and an upper component 12. The lower bed portion 16 and the upper component 12 are mechanically connected by a hinge 34. In other embodiments, the lower bed portion 16 and the upper component 12 are mechanically separated. In use, a collection substrate or sample card 50 such as a dried matrix spot card or dried blood spot card is placed within the lower bed portion 16 such that the collection regions of the sample card 50 are aligned with circular ridges 24 in the upper component 12 (e.g., as shown in FIG. 1B). When the upper component 12 is closed or lowered on to the lower bed portion 16, the circular ridges 24 are clamped directly onto the sample substrate surface (e.g., the surface of sample card 50) to define constrained surface extraction regions for each sample. The constrained surface extraction regions formed by the mechanical holder system 10 provide a substantially liquid tight seal around a portion of the collection substrate (e.g., at least about 90% of liquid dispersed onto the substrate is collected, at least about 95% of liquid dispersed onto the substrate is collected, at least about 98% of liquid dispersed onto the substrate is collected). A sample can be collected from one of the constrained surface extraction regions by sequentially dispensing and aspirating an extraction/electrospray solvent onto the sample surface in the extraction region using a pipette. After collection, analytes extracted from the sample are analyzed using mass spectrometry.

More particularly, the lower bed portion 16 is constructed to support and contain a collection substrate/sample card 50, for example, a dried matrix spot card or DBS card as shown in FIG. 1B. Exemplary collection substrates can be made of various pure paper materials and/or polymeric materials or other forms of membrane-like surfaces. In some examples, collection substrates such as matrix spot cards including blood spot cards include multiple sample locations each of which includes a separate collection regions 52 such as dried sample spots for analysis. In some examples, the lower bed portion 16 can include outer rails 32 configured to align the dried collection substrate with a cavity 14 in the lower bed portion 16 and secure the sample card 50 in the cavity 14. In such examples, the cavity 14 can be configured to have a size and shape that is similar or the same as the size and shape of a collection substrate. For example, dried matrix spot cards or similar surface supported analytical specimen cards have known widths ranging from 1 cm to 10 cm and known lengths ranging from 1 cm to 20 cm and the cavity 14 can be configured to be approximately the same size as the size of the sample card to allow the sample card to be inserted into the cavity 14 and secured therein. Providing a cavity 14 in the lower bed portion 16 can provide the advantage of securing the collection substrate in a known position within the mechanical holder system 10.

The lower bed portion 16 also includes a sample region 18. The sample region 18 is located within the cavity 14 in the lower bed portion 12 at a position that aligns with sample regions on the sample card 50. The sample region 18 includes a raised surface (e.g., raised in relation to the surface of other portions of the cavity 14) and includes multiple sample areas defined by ring-shaped depressions 20 in the sample region 18. More particularly, both the sample region 18 and a middle portion 22 of a particular sample area can be raised in relation to the surface of other portions of the cavity 14. The ring shaped depressions 20 are aligned with cylindrical fittings 24 in the upper hinged component 12 as described herein.

The upper component 12 provides a top surface that, when closed, encloses the sample card 50 within the mechanical holder system 10. The upper component 12 is connected to the lower bed portion 16 by a hinge. The upper component 12 can also include one or more locking mechanisms, e.g., locking mechanisms 29a, 29b, 29c, and 29d configured to secure the upper component 12 to the lower bed portion 16 when the upper component 12 is closed. The upper component 12 is configured to provide separate regions for analysis of each of the dried matrix spots 52 on the sample card 50. For example, as shown in FIGS. 1A-1C, the upper component 12 includes four (4) cylindrical fittings 24 each having a rigid perimeter surface 26 on the bottom which press down tightly on the dried matrix spot paper or substrate material of sample card 50 when the upper component 12 is lowered and clamped down to the lower bed portion 16. The rigid perimeter surface 26 can have a width of between 0.1 mm to 1 mm (e.g., 0.1 mm, 0.2 mm, 0.25 mm, 0.3 mm, 0.5 mm, 0.75 mm, or 1 mm). In some additional embodiments, the fittings 24 can be configured for analysis of a larger regions of a sample and include a rigid perimeter surface 26 having a width of between 2 mm to 5 mm (e.g., between about 2 mm and about 3 mm, between about 3 mm and about 4 mm, between about 4 mm and about 5 mm). In one exemplary embodiment, these fittings 24 are compression fittings made of PEEK (poly ether ether ketone), polymer, brass or stainless steel which are commercially available from Upchurch Scientific, Inc. or other suitable vendors. In some embodiments, the fittings 24 are made of a rigid plastic. The fittings 24 are held in place in the top portion of the described device by threaded holes (see, e.g., FIGS. 2A and 2B). The lower portion of the fittings 24 (e.g., the portion which extends from the lower surface of the upper component 12 to contact the sample card 50) are the shape of a compression fitting ferrule or similar configuration and provide a rigid, sharp and circular perimeter surface which may be pressed firmly onto, for example, a paper surface.

The fittings 24 include an opening sized to provide an adequate sample region and to receive a solvent delivery device (e.g., a pipette tip or extraction tip) for sample extraction. For example, the fittings can include an opening that is $\frac{1}{16}$ inch in diameter for smaller sample size applications of approximately 1 mm in diameter or and/or $\frac{1}{8}$ inch fittings which provide a sample extraction section of approximately 2-5 mm. Other fitting sizes are can also be used. Each of these fittings may be centered on the dried matrix spot region or sample application region on the paper or other substrate region to be analyzed.

As shown in FIG. 1C, the fittings 24 include an upper, open portion 40 configured to receive a solvent delivery device such as a pipette tip or an extraction tip that includes SPE sorbent or packing material. The upper, open portion 40 extends from the upper surface of the upper component 12 (e.g., the surface which is not in contact the sample card 50). For example, a pipette with an outside diameter of approximately 1 mm and an inside diameter of approximately one-half millimeter can enter a fitting opening 40 which is approximately 3 mm in diameter. Although the larger end of the solvent delivery device is approximately 4 mm, only the lower one-third of the solvent delivery device enters into the PEEK ferrule so there is ample space to accommodate the solvent delivery device within the PEEK ferrule fitting. In an automated system, the X, Y positioning (100 microns+/−50 microns) of the TriVersa NanoMate robot or its equivalent has sufficient precision and accuracy to reproducibly place the solvent delivery device (e.g., the pipette tip or extraction tip) into each fitting from sample to sample. The Z direction or closeness of approach by the tip of the solvent delivery device to the sample surface is similarly controlled by the robot to 100 microns+/−50 microns. Alternatively, one or more of the above actions can be performed manually.

As noted above, the upper component 12 includes one or more locking mechanisms, e.g., locking mechanisms 29a, 29b, 29c, and 29d configured to secure the upper component 12 to the lower bed portion 16 when the upper component 12 is closed. In the example shown in FIGS. 1A-1C, each of the locking mechanisms 29a, 29b, 29c, and 29d includes a moveable arm attached to the lower bed portion 16 by screws 28a, 28b, 28c, and 28d, respectively. The screws 28a, 28b, 28c, and 28d allow the locking mechanisms 29a, 29b, 29c, and 29d to be rotated and positioned above the upper component 12. The end of the arm portions each include a second screw 30a, 30b, 30c, and 30d to apply pressure to the upper surface of the upper component 12 when tightened. To lock the upper component 12 to the lower bed portion 16, the screws 30a, 30b, 30c, and 30d are tightened to press the rigid perimeter surface 26 of the fittings 24 on the upper surface into the ring shaped depressions 20 in the sample region 18 on the lower bed portion 16. A spacer can be included in the screw arrangements to ensure that screws 30a, 30b, 30c, and 30d are tightened in a manner to provide substantially uniform pressure onto the surface of the upper component 12.

Figure 2A:
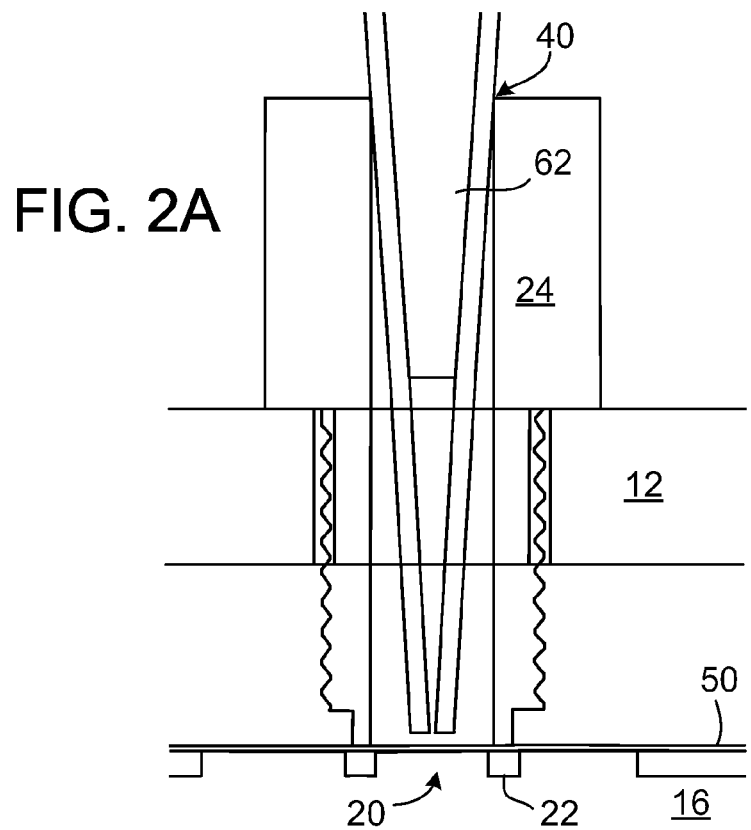
FIGS. 2A and 2B show an exemplary pipette inserted into a fitting in the mechanical holder.
Figure 2B:
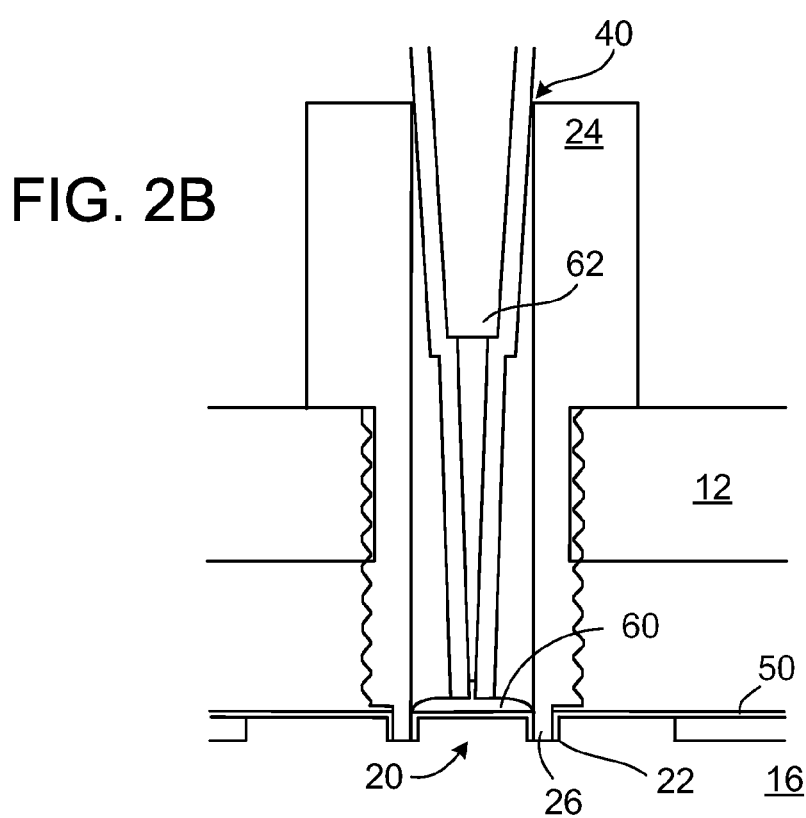

FIGS. 2A and 2B show a portion of the mechanical holder system 10 in a closed arrangement with the locking mechanisms 29a, 29b, 29c, and 29d disengaged and engaged, respectively. As shown in FIG. 2A, when the upper component 12 is lowered the rigid perimeter surface 26 of the cylindrical fittings 24 contacts a surface of the sample card 50. As shown in FIG. 2B, when the locking mechanisms 29a, 29b, 29c, and 29d are engaged, the cylindrical fittings 24 are clamped down tightly and uniformly, such that the circular rigid perimeter surface 26 of the cylindrical fittings 24 extends into the ring shaped depressions 22 in the sample region 18 and forms a liquid leak-tight seal between the surface of the fitting 24 and the tightly compressed paper surface of the card 50 supported by the aluminum lower bed portion 16. In some examples, the engagement of the locking mechanisms 29a, 29b, 29c, and 29d depresses the card by between about 0.015 inch to about 0.030 inch to form the liquid leak-tight seal.

After placement of the sample card 50 in the mechanical holder system 10 and engagement of the locking mechanisms 29a, 29b, 29c, and 29d, a robotic arm picks up a solvent delivery device (e.g., a conductive pipette tip or an extraction tip) and moves the solvent delivery device to the extraction solvent reservoir in order to pick up a 1-10 microliter aliquot of an extraction/spray solvent. In some additional embodiments, the fittings 24 can be configured for analysis of larger regions of a sample and 10-25 microliter aliquot of an extraction/spray solvent can be used. Then, the solvent delivery device is positioned within the fitting 24 above the surface of card 50 to form a micro liquid droplet or solvent pool maintained between the solvent delivery device and the sample surface. A sequence of repetitive dispense-aspirate steps affects an extraction of the sample surface. Then, the solvent delivery device is moved by the robot to the inlet of the microfabricated ESI chip and infusion nanoESI mass spectral acquisition is achieved employing either positive or negative ion detection. Exemplary solvent delivery devices are described, for example, in U.S. Ser. No. 12/960,037 filed Dec. 3, 2010, the contents of which is hereby incorporated by reference in its entirety Thus, an opening of the center portion of the fitting 24 confines the solvent extraction region to a defined area that is equal in size to the opening of the fitting. This allows a small volume of extraction solvent (e.g., 70% methanol, 30% water, 0.1% formic acid) to be dispensed into the fitting 24 and hence onto the surface of the sample card 50. The dispensed liquid forms a micro liquid droplet or small reservoir or pool of liquid solvent between the solvent delivery device and the sample surface such as a dried matrix spot (DXS). The osmotic dispersion of the solvent 60 can only spread to the inner wall surface of the fitting 24 which is clamped and pressed tightly to the sample surface. This restricted dispersion of the solvent limits the total volume of solvent required to extract chemicals from the DMS and hence maintains a higher concentration of analytes in the extract. The latter is beneficial for concentration-sensitive detectors such as electrospray mass spectrometry. In the absence of this confined region the extraction solvent could disperse to the extremities of the sample card and substantially dilute the sample and/or limit the quantity of material that may be aspirated back into the solvent delivery device for analysis. This can occur when the surface is hydrophyllic or highly absorptive of the solvent as is often the case in such applications.

The sample card holder forms reservoirs in the fittings 24 that have a minimum diameter of between about 0.5 to about 3 mm and the distance between the solvent delivery device (e.g., the pipette tip or extraction tip) and the sample surface is minimized to between about 0.5 to about 3 mm. In some additional embodiments, the fittings 24 can be configured for analysis of larger regions of a sample and have a minimum diameter of between about 3 mm to about 5 mm. Thus, in the example of fittings having a minimum diameter of between about 0.5 to about 3 mm the volume of solvent would range from about 0.98 cubic mm to about 21.2 cubic mm (volume=$3.14*r^2*$height). A portion of the respective total volume dispensed (a residual) will remain on the porous sample surface (card thickness might range from 0.01 mm to 0.5 mm), but the majority of the extract solution would be aspirated into the pipette tip or extraction tip for subsequent electrospray mass spectrometric analysis. For example, greater than 90% (e.g., greater than 90%, greater than 93%, greater than 95%, greater than 97%, greater than 98%) of the volume of dispensed solution would be aspirated into the pipette tip or extraction tip.

Alternatively or additionally, one can treat the sample surface with hydrophobic chemicals such as Rain X or similar products which are fluorocarbon or silicone sprays with water repellent properties for carpets, fabrics, etc. such that the solvent does not disperse throughout the paper or other absorbent surface. The described device with its confined rigid perimeter surface limits the unwanted dispersion of solvents through the sample surface substrate and precludes requiring additional treatment of the sample prior to analysis.

While the above description provides an example of a sample card holder with four fittings, other configurations are possible. For example, the sample card holder can include multiple rows of fittings forming a matrix of analysis locations. The number of fittings can vary based on the number of dried matrix spots or other analysis locations on the surface of the sample card to be analyzed. For example, the sample card holder can have fewer (e.g., one, two, three) fittings or a greater number of fittings (e.g., five, six, seven, eight, nine, ten, between 10-20, between 20-30, or greater than thirty fittings). In some additional examples, the sample card holder can include an 8×12 array of fittings. In some additional examples, the sample card holder can include 96 fittings to align with a 96-well plate arrangement. In some additional examples, the sample card holder can be configured to receive and house multiple sample cards such as dried matrix spot cards or dried blood spot cards. In such examples, the number of fittings on the upper surface is associated with the total number of analysis locations on the multiple dried matrix spot cards.

In some examples, the described sample card holder can be employed in a robotic solvent delivery and analysis system such as a robot similar to the NanoMate, TriVersa NanoMate (Advion BioSystems, Ithaca, N.Y. USA), or related automated device equipped with a mandrel which is capable of picking up a pipette tip or other disposable solvent delivery device such as an extraction tip. In one embodiment of the contemplated device a robotic device picks up a clean solvent delivery device, aliquots a small volume of extraction solvent (1-50 microliters) from a nearby solvent reservoir and then dispenses a portion of the extraction solvent within the sample card holder fitting such that a liquid junction is formed within the fitting between the sample surface and the solvent delivery device. This step affords an extraction of soluble compounds contained within the DBS sample surface into the extraction solvent contained within the solvent delivery device. Next the robotic device withdraws the extract solution from the DBS surface and delivers this solution containing dissolved chemicals/analytes to an analysis system such as a mass spectrometer.

In a representative example a sample collected from a collection substrate may be delivered to the inlet surface of a microfabricated chip (FIG. 3) which houses a multitude of ESI emitters/electrospray nozzle sprayers which individually produce in a sequential manner an electrospray plume directed to the inlet of an atmospheric pressure ionization (API) mass spectrometer. This system may produce mass spectral data which can be used for the qualitative or quantitative determination of chemicals/analytes of a wide diversity of types which may have been extracted from the sample card surface or similar substrate.

Figure 3:
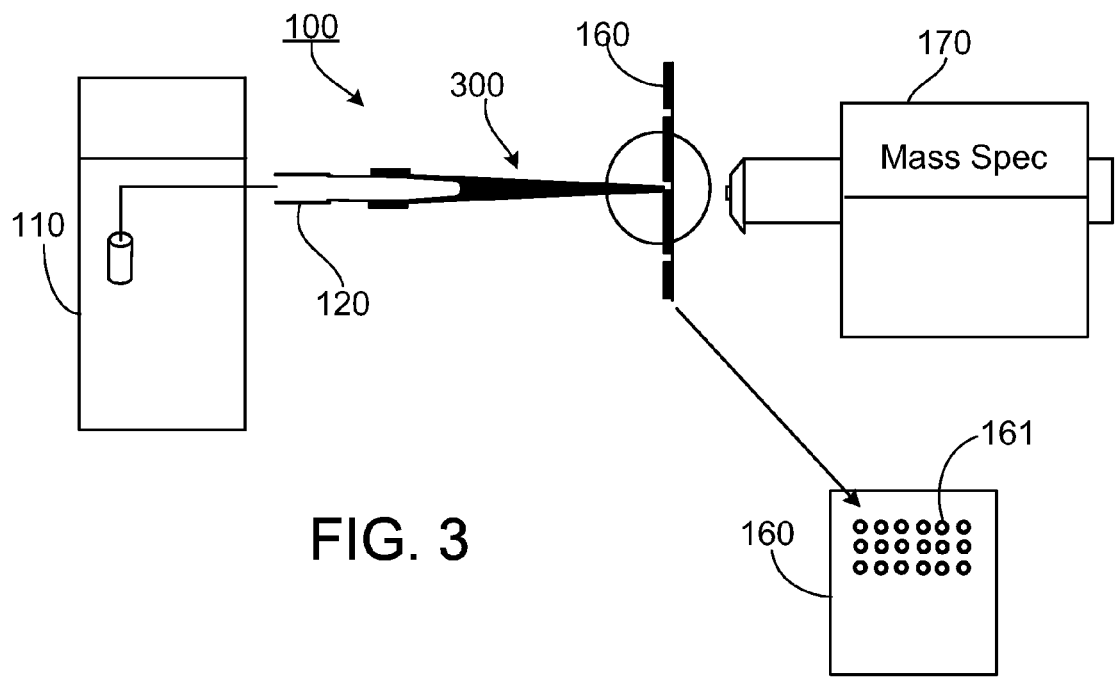
FIG. 3 is an exemplary system for delivering a sample solution to a chip-based electrospray device for forming an electrospray plume to introduce a sample into an orifice of a mass spectrometer.

More particularly, FIG. 3 shows an exemplary mass spectrometry system 100 used to identify the chemical composition of a compound based on the mass-to-charge ratio of charged particles derived from the compound. The mass spectrometry system 100 includes a solvent delivery system 110 that provides appropriate elution solvents, usually of high organic solvent content, to the extraction tip 300 (e.g., an extraction tip such as the tip described in U.S. Ser. No. 12/960,037 filed Dec. 3, 2010, the contents of which is hereby incorporated by reference in its entirety). In other embodiments, a pipette tip that does not include SPE sorbent or packing material can be used. While the example described in relation to FIG. 3 describes a solvent delivery system 110 capable of providing solvent and applying a vacuum, in some additional examples, a syringe can be used to provide the solvent to the extraction tip or pipette tip and to aspirate the solvent into the extraction tip or pipette tip. A mandrel 120 is used to connect the extraction tip 300 to the solvent delivery system 110. The solvent delivery system 110 may also include a device to provide a partial vacuum to the extraction tip 300 via a connection through the mandrel 120. In some embodiments, the slight vacuum can be applied using a syringe. The solvent delivery system 110 can be, for example, a liquid chromatograph such as a Waters nanoACQUITY, an Eksigent micro High Performance Liquid Chromatography (HPLC) system, or a Shimadzu liquid chromatograph equipped with a split flow arrangement with a reduced flow of mobile phase directed to a robot. The robot may be a system such as the NanoMate™ or TriVersa NanoMate™ (Advion BioSystems, Ithaca, N.Y. USA) equipped with the mandrel 120, which is capable of picking up a pipette tip or extraction tip from a multi-tip rack (e.g., 96 well plate, 384 well plate, 1536 well plate.). In some embodiments, the mandrel is a tapered metal tube having an inner diameter of, for example, from about 1 mm to about 5 mm. (e.g., about 2 mm, about 4 mm, about 6 mm, about 10 mm).

During use, the robot may deliver the extraction tip 300 that includes an SPE packing material to the openings in the mechanical holder system 10 to collect a sample from the surface of a sample card 50 (FIGS. 2A and 2B). In other embodiments, a pipette tip that does not include SPE packing material can be used. After collection of the sample, the robot may deliver the extraction tip 300 to the inlet surface of a microfabricated ESI chip 160 which houses a multitude of ESI emitters/electrospray nozzle sprayers 161. The end of the extraction tip 300 is aligned and positioned at an opening of the nozzle sprayers 161. Thus, during use a solvent is provided from the system 110 through the mandrel 120 and through the end of the extraction tip. As the solvent passes through the SPE packing material, the analytes retained therein are dissolved in the solvent. Fluidic or hydrostatic pressure from the solvent delivery system advances the eluting solvent or mobile phase and the dissolved analytes to the end of the extraction tip 300. The fluidic pressure dispenses the dissolved analytes from the SPE tip by directing the eluting solvent and dissolved analytes through the spray emitter 161 that has an applied voltage. As the eluting solvent and dissolved analytes are expelled from the nozzle sprayer 161, an electrospray (e.g., a mist of small, charged droplets that can range from sub-micron size under nanoelectrospray conditions to about 1-10 µm across) is formed. The electrospray is typically generated at or near atmospheric pressure and provides highly charged droplets of the solution containing analytes. For example, microfabricated ESI chip 160 may include a 20×20 array of nozzle sprayer 161 (or an array of 5×5 nozzles or 7×7 nozzles or other similar arrangements of spray emitters in a microfluidic chip arrangement) having openings of between 2-50 µm in diameter (e.g., 2 µm, 5 µm, 10 µm, 30 µm or 50 µm in diameter). Other types of sprayers including a spray probe or tube devices and a microfabricated sprayer device can also be used. For example, a pipette tip that does not include SPE packing material can be used. In other examples, rather than providing a solvent through the tip to force the analytes to be expelled through the sprayer 161, a slight Nitrogen gas pressure can be applied to the tip and to the several microliters of extract within the tip which pushes/infuses the solvent extract through the ESI chip 160 for analysis.

Figure 4:
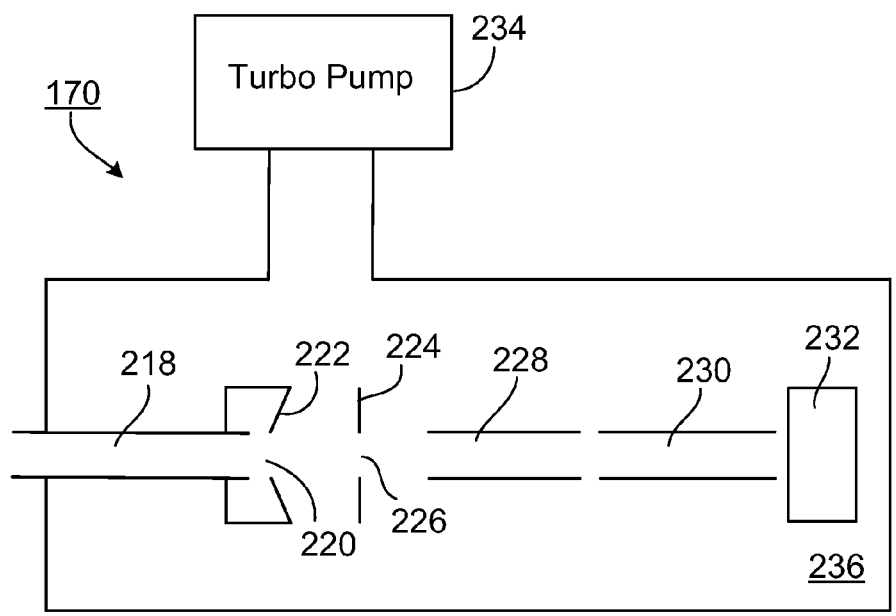
FIG. 4 shows a schematic representation a mass spectrometer.

Upon passage through the nozzle sprayer 161 the electrospray is directed towards the inlet orifice of an atmospheric pressure ionization (API) mass spectrometer 170. FIG. 4 shows a schematic representation of the components within mass spectrometer 170. The electrospray droplets enter into an atmospheric pressure interface (API), such as a capillary 218 (while this example describes a heated capillary inlet, other inlets can be used), that directs the ions from the electrospray into a vacuum portion 236 of the mass spectrometry system 170. As the droplets from the electrospray travel through the capillary 218, desolvation occurs such that ions emerge from an exit 220 of the capillary 218. The ions are directed through a skimmer 222 and the ions that emerge from the skimmer 222 are focused by a set of lenses 224 and into an ion optics region which may be a multipole region 228 or related or other type of lens focusing system. This multipole or ion optics region is typically operated in the Rf-only mode and may be composed of a quadrupole, hexapole, octapole or similar ion optics device. In embodiments in which a hexapole device is used as the multipole region 228, the ions are further guided through a quadrupole analyzer 230 or other mass analyzer capable of resolving ions with a mass-to-charge ratio and into a detector 232. The detector 232 amplifies the weak ion current signal of the sample ions. The detector may include an electron multiplier, photo multiplier or other suitable detector.

The solvent delivery from the solvent delivery device may range from as low as 20 nL/min or as high as 50 microliters/min. The analyte(s) eluted from the solvent delivery device may be ionized by an electrospray process or other available atmospheric pressure ionization techniques such as atmospheric pressure chemical ionization (APCI) and detected by mass spectrometry to produce either a full-scan electrospray mass spectrum in either the positive ion mode or the negative ion mode depending upon the chemistry of the eluted analyte(s) from the solvent delivery device. Alternatively, the detected analyte(s) may be detected and analyzed by other common mass spectrometric acquisition modes such as full-scan mass spectral acquisition, full-scan MS/MS acquisition, neutral loss scans, precursor ion scans, selected reaction monitoring (SRM), multiple reaction monitoring (MRM), selected ion monitoring (SIM) or other common, modern acquisition modes of mass spectrometry. Applications that may benefit from this approach include pharmaceutical drug discovery and development, clinical diagnostics to monitor markers of disease, Vitamin D, its analogs and other steroids, amino acids, small drug compounds and their metabolites, antibiotics, peptides and proteins, inborn markers of metabolism such as carnitines, vitamins, forensic compounds, chemical warfare agents, nutritional supplements, pesticides and other potentially toxic chemicals on food surfaces, etc.

In some embodiments, the system can be fully automated. In a fully automated system, the system would introduce the sample card or sample surface to be analyzed followed by robotic analysis as described above and finally an automated procedure for removing the sample card post-analysis to make way for the next sample card. In some additional embodiments, the system may be operated in a manual mode in which a user manually performs one or more the actions described herein.

While in some of the examples above a micro liquid junction is formed between the solvent delivery device and the sample card, in some embodiments a micro liquid junction is not formed and instead the liquid disperses into the paper/substrate material like the wetting of a sponge. In this case given sufficient liquid in the wetted surface the pipette tip still aspirates liquid from the wetted sponge-like surface.

While in some of the examples above the lower bed portion 16 and the upper component 12 are mechanically connected by a hinge 34, in other embodiments, the lower bed portion 16 and the upper component 12 are mechanically separated and are used in a format similar to that of a press.

While at least some of the description above focuses on the analysis of dried blood spots, dried spots of other samples of interest (e.g., urine, plasma, saliva, feces, milk, food, fruits, vegetables, etc.) can be analyzed using the systems and methods described herein.

What is claimed is:

1. A system, comprising:
a lower portion configured to house an sample card;
an upper portion mechanically connected to the lower portion, the upper portion including an array of fittings configured such that when the upper portion and the lower portion are in a closed position, a substantially liquid tight seal is formed around multiple, different portions of the sample card.

2. The system of claim 1, wherein the liquid tight seal is configured to confine at least 95% of the extraction solvent within the walls of the fitting.

3. The system of claim 1, wherein the sample card that includes a dried sample.

4. The system of claim 1, wherein the fittings are configured to receive a solvent delivery device and include a rigid lower perimeter edge.

5. The system of claim 1, wherein the fittings are configured to receive a solvent delivery device capable of delivering an extraction solvent for extracting chemicals from the sample substrate material.

6. The system of claim 1, wherein the fittings are configured to receive a pipette tip.

7. The system of claim 1, wherein the fitting comprises PEEK, polymer, brass or stainless steel with a rigid lower circular perimeter edge capable of making a leak-tight seal when clamped down upon the sample card without cutting a disk from the sample card.

8. The system of claim 1, further comprising a robotic device configured to extract analytes from the sample card to form a solution from a surface of the sample card using a solvent delivery device which can then be withdrawn from the surface and delivered to a mass spectrometer.

9. The system of claim 1 wherein the fitting is configured such that extraction solvent introduced into the fitting is substantially confined within the walls of the fitting.

10. The system of claim 1, further comprising a locking mechanism configured to compress the sample card.

11. The system of claim 10, wherein the locking mechanism is configured to depress the sample card by between about 0.015 inch to about 0.030 inch to form the substantially liquid tight seal.

12. The system of claim 10, wherein the locking mechanism comprises one or more screws.

13. The system of claim 1, wherein the fitting comprises PEEK with a rigid lower circular perimeter edge capable of making a leak-tight seal when clamped down upon the sample card without cutting a disk from the sample card.

14. The system of claim 1, wherein the fitting comprises brass or stainless steel with a rigid lower circular perimeter edge capable of making a leak-tight seal when clamped down upon the sample card without cutting a disk from the sample card.

15. The system of claim 1, wherein the array of fittings comprises an array of 96 fittings.

16. The system of claim 1, wherein the liquid tight seal is configured to confine at least 98% of the extraction solvent within the walls of the fitting.

17. The system of claim 1, wherein the array of fittings comprises at least four fittings.

18. The system of claim 1, wherein the sample card comprises a porous surface.

19. The system of claim 1, wherein the fittings comprise cylindrical fittings with a diameter of 0.1 mm to 1 mm.

20. The system of claim 1, wherein the fittings comprise cylindrical fittings with a diameter of 2 mm to 5 mm.

* * * * *